United States Patent [19]

Packard et al.

[11] Patent Number: 5,421,208
[45] Date of Patent: Jun. 6, 1995

[54] INSTANTANEOUS VOLUME MEASUREMENT SYSTEM AND METHOD FOR NON-INVASIVELY MEASURING LIQUID PARAMETERS

[75] Inventors: Warren J. Packard, Chicago; Kenneth E. Pawlak, Vernon Hills, both of Ill.

[73] Assignee: Baxter International Inc., Deerfield, Ill.

[21] Appl. No.: 245,781

[22] Filed: May 19, 1994

[51] Int. Cl.⁶ .............................................. G01F 1/00
[52] U.S. Cl. ..................................... 73/861; 73/861.39; 417/63; 417/43; 417/384; 417/395
[58] Field of Search .......................... 673/861, 861.39; 417/63, 43, 384, 395

[56] References Cited

U.S. PATENT DOCUMENTS

| | | | |
|---|---|---|---|
| 2,827,853 | 3/1958 | Bradley | 417/63 |
| 2,889,780 | 6/1959 | Binford | 417/43 |
| 3,344,667 | 10/1967 | Maltby | 73/239 |
| 3,657,925 | 4/1972 | Gross | 73/239 |
| 4,778,451 | 10/1988 | Kamen | 417/395 |
| 4,808,161 | 2/1989 | Kamen | |
| 5,027,661 | 7/1991 | Desaulniers et al. | 73/861 |
| 5,115,682 | 5/1992 | Feiler | 73/861 |

Primary Examiner—Richard E. Chilcot, Jr.
Assistant Examiner—Jewel V. Artis
Attorney, Agent, or Firm—Thomas S. Borecki; Charles R. Mattenson; Robert M. Barrett

[57] ABSTRACT

A non-invasive technique and system is provided for measuring flow of liquid driven by a flexible diaphragm of a membrane pump (18). Flow, pressure and/or temperature of a gas, such as air, used to drive the pump (18) is continuously monitored. Instantaneous volume of liquid being pulled into or out of a chamber of the pump (18) can be calculated from measured values of the gas used to drive the pump (18). Sensors (10, 12 and/or 14) are used to measure values relating to the gas. The sensed parameters are concurrently monitored and continuously determine the amount of gas flowing to and from the diaphragm of the membrane pump (18) utilized to move liquid within a liquid pathway. The measurements may then be used to calculate the instantaneous flow rate of the liquid.

14 Claims, 1 Drawing Sheet

INSTANTANEOUS VOLUME MEASUREMENT SYSTEM AND METHOD FOR NON-INVASIVELY MEASURING LIQUID PARAMETERS

BACKGROUND OF THE INVENTION

The present invention relates generally to a system and a method for measuring flow of a liquid. More specifically, the present invention relates to a non-invasive system and a method for measuring liquid flow driven by a flexible diaphragm, membrane pump, bellows, or piston.

Peritoneal dialysis (PD) is a generally known system requiring periodic infusion of sterile aqueous solutions into a peritoneal cavity of a patient. The infused solution is generally known as a peritoneal dialysis solution or dialysate.

Many types or forms of peritoneal dialysis are generally known, such as Continuous Ambulatory Peritoneal Dialysis (CAPD), Continuously Cycling Peritoneal Dialysis (CCPD), Automated Peritoneal Dialysis (APD), Intermittent Peritoneal Dialysis (IPD) and Tidal Peritoneal Dialysis (TPD).

In continuous ambulatory peritoneal dialysis (CAPD), a patient performs the dialysis manually about four times a day. During CAPD, the patient drains spent peritoneal dialysis solution from his peritoneal cavity. The patient then infuses fresh peritoneal dialysis solution into his peritoneal cavity. The drain and fill up procedure usually takes approximately one hour.

Automated peritoneal dialysis (APD) uses a machine, called a cycler, to automatically infuse, dwell, and drain peritoneal dialysis solution to and from the patient's peritoneal cavity. APD can be performed at night while the patient is asleep freeing the patient from day-to-day demands of CAPD during his waking and working hours.

APD typically lasts for several hours beginning with an initial drain cycle to empty the peritoneal cavity of spent dialysate. The APD sequence proceeds through a succession of fill, dwell and drain phases which follow one after the other. Each fill/dwell/drain sequence is called a cycle.

During the fill phase, the cycler transfers a predetermined volume of fresh, warm dialysate into the peritoneal cavity of the patient. The dialysate remains within the peritoneal cavity for a time period. During the drain phase, the cycler removes the spent dialysate from the peritoneal cavity. The number of fill/dwell/drain cycles that are required during a given APD session depends upon the total volume of dialysate prescribed for the patient's APD regime.

Continuously cycling peritoneal dialysis (CCPD) is one commonly used APD method. During each fill/dwell/drain phase of CCPD, the cycler infuses a prescribed volume of dialysate. After a prescribed dwell period, the cycler completely drains the liquid volume from the patient, leaving the peritoneal cavity empty. Typically, CCPD employs six fill/dwell/drain cycles to achieve a prescribed therapy volume.

After the last prescribed fill/dwell/drain cycle in CCPD, the cycler infuses a final fill volume. The final fill volume dwells in the patient through the day. The final fill volume is drained at the outside of the next CCPD session in the evening. The final fill volume can contain a different concentration of dextrose than the fill volume of the successor CCPD fill/dwell/drain fill cycles the cycler provides.

Intermittent peritoneal dialysis (IPD) is another form of APD. IPD is typically used in acute situations when a patient suddenly enters dialysis therapy. IPD can also be used when a patient requires IPD, but cannot undertake the responsibilities of CCPD. IPD involves a series of fill/dwell/drain cycles. The cycles in IPD are typically closer in time than in CCPD. In addition, IPD does not include a final fill phase. Rather, the patient's peritoneal cavity is left free of dialysate in-between APD therapy sessions.

Tidal peritoneal dialysis (TPD) is another form of APD. TPD includes a series of fill/dwell/drain cycles. Unlike CCPD, TPD does not completely drain dialysate from the peritoneal cavity during each drain phase. Instead, TPD establishes a base volume during the first fill phase and drains only a portion of the volume during the first drain phase. Subsequent fill/dwell/drain cycles infuse then drain a replacement volume on top of the base volume, except for the last drain phase. The last drain phase removes all dialysate from the peritoneal cavity.

Measurement of flow rate or other parameters of a liquid, either invasively or non-invasively is, of course, generally known. Peritoneal dialysis requires a technique for measuring flow rate that does not compromise sterility. Typically, the technique employed for such measurements is non-invasive. One common technique for non-invasively measuring flow rate in peritoneal dialysis is by differentiation of weight measurements. This technique uses a load cell which supports the supply bag and the drain bag to monitor weight differentials therebetween and to calculate rate therefrom. Such a technique enables one to derive instantaneous volume measurement.

In some applications or environments, however, instantaneous flow rate of a liquid must be determined within a sterile disposable without the use of gravity dependent weight measurements. In such environments, such as peritoneal dialysis procedures implementing a cassette-based system including a flexible diaphragm pump, a non-invasive technique is required for measuring and/or constantly monitoring flow rate going to or coming from a patient.

A need, therefore, exists for a system and a method for non-invasively measuring flow of a liquid driven by a flexible diaphragm or membrane pump to determine instantaneous flow rate and measurements derived therefrom.

SUMMARY OF THE INVENTION

The present invention provides a system and a method for measuring flow of liquid non-invasively. To this end, the present invention monitors parameters of gas used to drive a membrane pump. From these measurements, instantaneous volume of liquid being pulled into or out of the pump chamber can be calculated.

In an embodiment, a system is provided for monitoring a liquid driven by a pump and calculating a parameter related to the liquid. The system comprises means for measuring at least one variable related to gas used to drive the pump. Means for calculating instantaneous flow rate of the liquid flowing into or out of the pump from the at least one measured parameter is further provided.

In an embodiment, the means for calculating further calculates instantaneous liquid volume from the instantaneous flow rate.

In an embodiment, the means for measuring measures at least flow of the gas and pressure of the gas. The means for measuring may further measure temperature of the gas.

In an embodiment, the means for measuring non-invasively measures at least one variable.

In an embodiment, the liquid driven by the pump flows into or out of a sterile disposable.

In another embodiment of the present invention, a system is provided for measuring a liquid-related value of a liquid driven by a pump. The system comprises first sensing means for sensing flow of gas for driving the pump and second sensing means for sensing pressure of the gas for driving the pump. Further, calculating means determines instantaneous flow rate of the liquid flowing into or out of the pump from the sensed gas flow and the sensed pressure.

In an embodiment, the system further comprises third sensing means for sensing temperature of the gas for driving the pump.

In another embodiment of the present invention, a method is provided for non-invasively monitoring parameters of a liquid driven by a pump. The method comprises the steps of: measuring at least one value related to gas required for driving the pump; and calculating instantaneous flow rate of the liquid flowing into or out of the pump based on the at least one measured value.

In an embodiment, the at least one measured values include gas flow and gas pressure.

In an embodiment, the method further comprises the step of measuring temperature of the gas driving the pump. In this embodiment, the flow rate is calculated by using the measured temperature, gas flow and gas pressure.

In an embodiment, the method further comprises the step of calculating instantaneous liquid volume from the instantaneous flow rate.

In an embodiment, the method further comprises the step of pumping the liquid into or out of a sterile disposable.

It is, therefore, an advantage of the present invention to provide a system and a method for non-invasive measuring of flow of a liquid.

Another advantage of the present invention is to provide a system and a method for measuring flow of a liquid with a fast response time.

Further, an advantage of the present invention is to provide a system and a method for measuring the flow of liquid with low hysteresis within the system.

Still further, an advantage of the present invention is to provide a system and a method for measuring flow of a liquid requiring few components.

Yet another advantage of the present invention is to provide a system and a method for measuring instantaneous volume moving into or out of a pumping chamber.

Moreover, an advantage of the present invention is to provide a system and a method which simply incorporates additional pumps.

Additional features and advantages of the present invention are described in, and will be apparent from, the detailed description of the presently preferred embodiments and from the drawings.

DETAILED DESCRIPTION OF THE PRESENTLY PREFERRED EMBODIMENTS

The present invention generally provides a system and a method for monitoring a liquid driven by a pump. To this end, sensors are provided for measuring parameters of gas used to drive a pump. From measurement of the parameters, flow of liquid and instantaneous volume of liquid being driven into or out of a pump chamber can be calculated. As a result, non-invasive measurement of liquid flow within a sterile environment is achieved.

The preset invention is described with reference to air as the gas used for the system. Any gas, however, could be used in the system of the present invention. Further, the present invention is applicable to any fluid handling or fluid administration system and should not be construed as limited to fluid handling for peritoneal dialysis. Rather, the present invention may be implemented in any fluid handling system, such as, but not limited to, hemodialysis and other medical applications, food applications, chemical applications, and the like.

Figure 1:
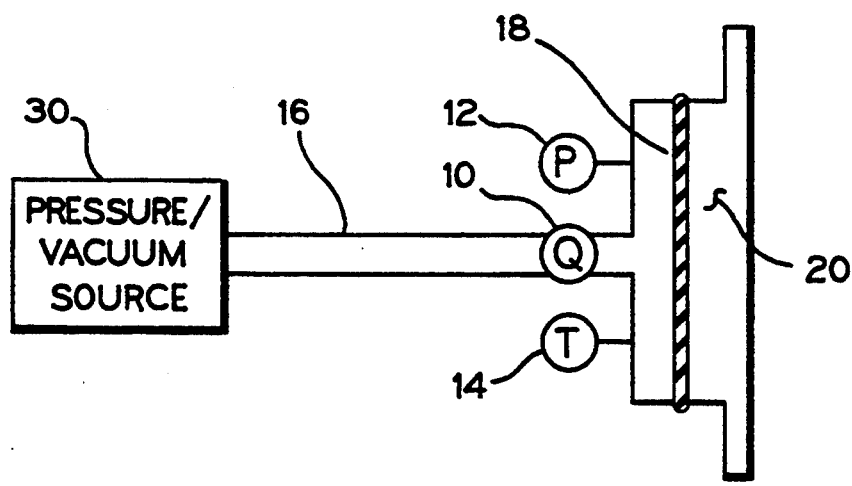
FIG. 1 illustrates a schematic diagram of a system for measuring flow of liquid driven by a flexible diaphragm or membrane pump.

Referring now to the drawings, FIG. 1 illustrates a gas flow sensor 10, a pressure sensor 12 and a temperature sensor 14. The sensors are also designated Q, P and T for better understanding of the invention, particularly for comprehension of the calculation leading to instantaneous volume measurement.

The sensors 10, 12 and 14 sense respective parameters of a gas flow stream 16. A liquid in a sterile disposable is driven by a membrane pump 18. The membrane pump 18 provides controlled pumping of gas to and from the liquid pathway. Membrane pumps are generally known and described in the U.S. patent application Ser. No. 08/027,328, entitled "Peritoneal Dialysis Systems and Methods Employing a Liquid Distribution and Pumping Cassette that Emulates Gravity Flow", the disclosure of which is fully incorporated by reference herein.

As illustrated in FIG. 1, the gas flow sensor 10, the pressure sensor 12, and the temperature sensor 14 are located immediately upstream of the flexible diaphragm or the membrane pump 18. Positive and negative pressures are applied to the membrane pump 18 which causes the liquid 20 to be moved within the liquid pathway.

The three sensors 10, 12 and 14 are monitored concurrently to determine an amount of gas flowing to and from the membrane of the membrane pump 18. The sensed measurements may, in turn, be manipulated to determine the flow of liquid, instantaneous flow rate of the liquid and instantaneous volume measurements of the liquid as will be set forth hereinafter.

The instantaneous liquid volume to/from the diaphragm can be calculated by derivation of the instantaneous gas flow to the diaphragm or membrane of the membrane pump 18. The result is continuously integrated over time to generate uninterrupted volumetric flow information. That is, in mathematical terms, continuous updating of the value of dV/dt from the readings of the sensors 10, 12 and 14 and subsequent calculations, the value of instantaneous liquid volume in the diaphragm may be calculated as follows:

$$V_t = \int_0^t \left(\frac{dV}{dt}\right) dt$$

As a computer algorithm, this equation can be solved through numerical integration. This equation can, of course, take many forms. The most basic form is as follows:

$$V_{t+1} = V_t + \Delta V$$

In the above equation, $\Delta V$ is the instantaneous gas volume difference calculated at each time interval. $\Delta V$ can be obtained by continuously monitoring the instantaneous values for pressure P, temperature T and gas mass m and solving the instantaneous change in gas volume $\Delta V$ as follows:

$$\Delta V = V_t \left( \frac{\Delta m}{m} + \frac{\Delta T}{T} - \frac{\Delta P}{P} \right)$$

The total volume delivered to or from a patient or other sterile environment can be continuously updated by simply adding the amount of volume moved $\Delta V$ to the amount of fluid or volume of fluid $V_t$ currently in the patient or other sterile environment. From this, an instantaneous volume measurement system (IVMS) equation can be derived as follows:

$$V_{t+1} = V_t + \Delta V, \text{ i.e., } V_t = \int_0^t \frac{dV}{dt} dt$$

One form of the IVMS equation is derived by differentiating the ideal gas law with respect to time and reintegrating the result to obtain an equation for change in volume with respect to changes in pressure, temperature and gas flow. Initially, the ideal gas law is provided as follows:

$$PV = mR_{gas}T$$

The derivative of the ideal gas law is expanded as follows:

$$\frac{dV}{dt} = R_{gas}\frac{T}{P}\frac{dm}{dt} + \frac{mR_{gas}}{P}\frac{dT}{dt} - \frac{mR_{gas}T}{P^2}\frac{dP}{dt}$$

Volume may then be determined by integration as follows:

$$V = \int \frac{dV}{dt} dt$$

$$V = \int \left( \frac{R_{gas}T}{P}\frac{dm}{dt} + \frac{mR_{gas}}{P}\frac{dT}{dt} - \frac{mR_{gas}T}{P^2}\frac{dP}{dt} \right) dt$$

$$V = \int \frac{R_{gas}T}{P} dm + \int \frac{mR_{gas}}{P} dT - \int \frac{mR_{gas}T}{P^2} dP$$

For implementing the above as a computer algorithm, the above formula can be written as a difference equation with the simplest form of this type of equation being as follows:

$$V_{t+1} = V_t + \frac{R_{gas}T}{P}\Delta m + \frac{mR_{gas}}{P}\Delta T - \frac{mR_{gas}T}{P^2}\Delta P$$

$$V_{t+1} = V_t \left( 1 + \frac{\Delta m}{m} + \frac{\Delta t}{t} - \frac{\Delta P}{P} \right)$$

Of course, a number of possible variants to the above equation and design for calculating instantaneous volume measurement may be derived. The equation set forth above can be modified to provide a higher order solution. Such an implementation would provide improved accuracy at the expense of greater computation time.

Another alternative embodiment for calculating the instantaneous volume of the liquid eliminates the temperature sensor 14 from the system. Temperature of the gas flow may typically only exhibit a second or third order influence on the overall accuracy of the instantaneous volume measurement system equation. When this is the case, the temperature sensor 14 can be eliminated without any significant loss in accuracy of the measurement. Then, when the temperature sensor is removed from the system, the above equation can be modified to provide a higher order solution without a substantial impact on the computation time, i.e. greater computation time.

Figure 2:
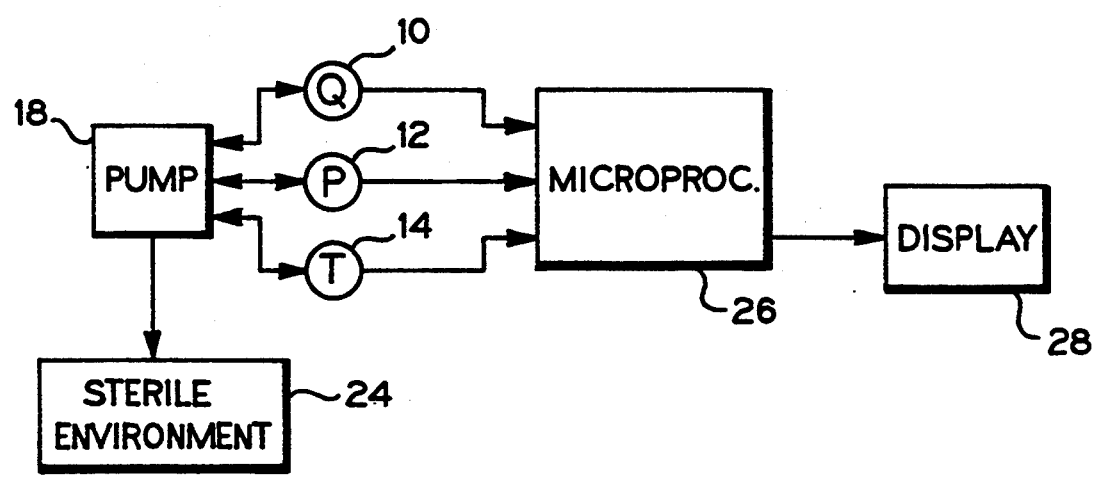
FIG. 2 illustrates a black-box diagram of the components for non-invasively measuring flow of liquid driven by a pump and calculating of the flow rate and instantaneous volume.

Referring now to FIG. 2, a pump 18 is illustrated for driving a membrane or diaphragm of the pump 18 at an interface of a liquid pathway to a sterile environment 24. Gas is driven by or drawn from the pump 18 by a pressure/vacuum source 30 which, in turn, pumps liquid or slows pumping of liquid within the sterile environment 24.

The sensors 10, 12 and 14 monitor gas flow, pressure and/or temperature, respectively, of the system. The sensors 10, 12 and 14 provide signals concurrently to a microprocessor 26 for calculating the instantaneous volume measurement of the flow of liquid based on the sensed parameters of the gas flow driving the pump 18. The instantaneous volume measurement is calculated as set forth above using the IVMS equation.

The calculated instantaneous volume measurement may be displayed on a display 28. As a result, for example, an operator may view the display to operate or otherwise alter the system accordingly.

The present invention is particularly adaptable for dialysis machines using one or more of the known dialysis procedures. That is, a cassette having a plurality of lines into the cassette, typically five lines, a plurality of valves and two chambers may implement the system and method for instantaneous volume measurement disclosed by the present invention. The cassette having a plurality of lines, a plurality of valves and multiple chambers is set forth in commonly assigned U.S. patent application Ser. No. 08/027,328 entitled "Peritoneal Dialysis Systems and Methods Employing a Liquid Distribution and Pumping Cassette that Emulates Gravity Flow", the disclosure of which is fully incorporated herein by reference.

It should be understood that various changes and modifications to the presently preferred embodiments described herein will be apparent to those skilled in the art. Such changes and modifications may be made without departing from the spirit and scope of the present invention and without diminishing its attendant advantages. It is, therefore, intended that such changes and modifications be covered by the appended claims.

We claim:

1. A system for monitoring a liquid driven by a pump and calculating a parameter related to the liquid, the system comprising:
   providing a gas to drive the pump;
   means for measuring flow and pressure of the gas used to drive the pump; and
   means for calculating instantaneous flow rate of the liquid flowing into or out of the pump from the measured flow and pressure of the gas.

2. The system of claim 1 wherein the means for calculating further calculates instantaneous liquid volume from the instantaneous flow rate.

3. The system of claim 1 wherein the means for measuring measures temperature of the gas.

4. The system of claim 1 wherein the means for measuring non-invasively measures the at least one variable.

5. The system of claim 1 wherein the liquid driven by the pump flows into or out of a sterile disposable.

6. A system for measuring a liquid-related value of a liquid driven by a pump, the system comprising:
   means for providing a gas to drive the pump;
   first sensing means sensing flow of the gas driving the pump;
   second sensing means sensing pressure of the gas driving the pump; and
   calculating means determining instantaneous flow rate of the liquid flowing into or out of the pump from the sensed gas flow and the sensed pressure.

7. The system of claim 6 further comprising:
   third sensing means for sensing temperature of the gas for driving the pump.

8. The system of claim 7 wherein the calculating means determines instantaneous flow rate from the sensed gas flow, the sensed pressure and the sensed temperature.

9. The system of claim 6 wherein the means for calculating determines instantaneous volume from the determined instantaneous flow rate of the liquid.

10. A method for non-invasively monitoring parameters of a liquid driven by a pump, the method comprising the steps of:
    providing a gas to drive the pump;
    measuring gas flow and gas pressure of the gas driving the pump; and
    calculating instantaneous flow rate of the liquid flowing into or out of the pump based on the at least one measured value.

11. The method of claim 10 further comprising the step of:
    measuring temperature of the gas driving the pump.

12. The method of claim 11 wherein the flow rate is calculated by using the measured temperature, gas flow and gas pressure.

13. The method of claim 10 further comprising the step of:
    calculating instantaneous liquid volume from the instantaneous flow rate.

14. The method of claim 10 further comprising the step of:
    pumping the liquid into or out of a sterile disposable.

* * * * *